United States Patent
Chen et al.

(10) Patent No.: US 9,687,563 B2
(45) Date of Patent: Jun. 27, 2017

(54) PH-SENSITIVE PEPTIDES AND THEIR NANOPARTICLES FOR DRUG DELIVERY

(71) Applicant: THE TRUSTEES OF THE UNIVERSITY OF PENNSYLVANIA, Philadelphia, PA (US)

(72) Inventors: I-Wei Chen, Swarthmore, PA (US); Hoon Choi, Newtown Square, PA (US); Rong Zhou, Cherry Hill, NJ (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 0 days.

(21) Appl. No.: 14/914,787

(22) PCT Filed: Aug. 13, 2014

(86) PCT No.: PCT/US2014/050881
§ 371 (c)(1),
(2) Date: Feb. 26, 2016

(87) PCT Pub. No.: WO2015/031059
PCT Pub. Date: Mar. 5, 2015

(65) Prior Publication Data
US 2016/0213790 A1    Jul. 28, 2016

Related U.S. Application Data

(60) Provisional application No. 61/869,944, filed on Aug. 26, 2013.

(51) Int. Cl.
| | | |
|---|---|---|
| *A61K 47/48* | (2006.01) | |
| *A61K 9/51* | (2006.01) | |
| *C12N 15/11* | (2006.01) | |
| *A61K 31/337* | (2006.01) | |
| *A61K 31/416* | (2006.01) | |
| *A61K 31/433* | (2006.01) | |
| *C07K 7/08* | (2006.01) | |
| *C12N 15/113* | (2010.01) | |

(52) U.S. Cl.
CPC ...... *A61K 47/48884* (2013.01); *A61K 9/5169* (2013.01); *A61K 31/337* (2013.01); *A61K 31/416* (2013.01); *A61K 31/433* (2013.01); *A61K 47/48215* (2013.01); *A61K 47/48315* (2013.01); *A61K 47/48807* (2013.01); *A61K 47/48907* (2013.01); *C07K 7/08* (2013.01); *C12N 15/111* (2013.01); *C12N 15/113* (2013.01); *C12N 2310/14* (2013.01); *C12N 2310/141* (2013.01); *C12N 2310/3513* (2013.01); *C12N 2320/32* (2013.01); *C12N 2320/51* (2013.01)

(58) Field of Classification Search
None
See application file for complete search history.

(56) References Cited

U.S. PATENT DOCUMENTS

| | | |
|---|---|---|
| 2010/0286069 A1 | 11/2010 | Yang et al. |
| 2010/0286070 A1 | 11/2010 | Verheyden et al. |
| 2011/0038939 A1 | 2/2011 | Lvov et al. |
| 2011/0059181 A1 | 3/2011 | Hu et al. |
| 2013/0041133 A1 | 2/2013 | Aaronson et al. |

OTHER PUBLICATIONS

Andreev et al., PNAS, 107(9):4081-86 (2010).
Blackburn et al., Bioconjug Chem, 20(5):960-68 (2009).
Borza and Morgan, J Biolog Chem, 273(10):5493-99 (1998).
Danhler et al., J Controlled Release, 140:166-73 (2009).
International Search Report dated Jan. 21, 2015, from PCT International Application No. PCT/US2014/050881.
International Preliminary Report and Written Opinion for PCT/US2014/050881 mailed Mar. 10, 2016.
Danhler et al., Journal of Controlled Release, 148:135-46 (2010).
Huh et al., Macromolecular Research, 20:224-33 (2012)..
Li et al., Advanced Drug Delivery Reviews 56:967-85 (2004).

*Primary Examiner* — Thomas S Heard
(74) *Attorney, Agent, or Firm* — RatnerPrestia

(57) ABSTRACT

A new nanoscale carrier made by one or more pH-sensitive peptides is provided for delivery of a biologically active substance. The peptides are composed of pH-sensitive hydrophilic and hydrophobic amino acids in the backbone. As the pH environment changes from physiological pH level to a weakly acidic environment such as near a tumor site (pH~6.5-6.9), the peptides may dissolve, releasing the biological substance. Also provided are the delivery methods and related kits.

37 Claims, 13 Drawing Sheets

Peptide: HFFHGHFFHGHFFHGKK (a)

(b)

(a)

(b)

(a)

(b)

(a)

(b)

PH-SENSITIVE PEPTIDES AND THEIR NANOPARTICLES FOR DRUG DELIVERY

CROSS-REFERENCE TO RELATED APPLICATION

This application is a U.S. national phase application of International Application No. PCT/US2014/050881, filed Aug. 13, 2014 claiming the benefit of U.S. Provisional Application No. 61/869,944, entitled "PH-SENSITIVE PEPTIDES AND THEIR NANOPARTICLES FOR DRUG DELIVERY" filed 26 Aug. 2013, the contents of each of which are incorporated herein by reference in their entireties and for all purposes.

REFERENCE TO U.S. GOVERNMENT SUPPORT

This work is supported by grants from the Department of Defense, Army Research Office (Award Numbers W81XWH-1Q10320, & W81XWH-1Q10604). The United States has certain rights in the invention.

BACKGROUND OF THE INVENTION

Disease states such as cancer may present with sites of a body having pH ranges below that of a neutral physiological pH between 7.0 and 7.4. These sites may include, for example, tumors. Targeting these sites may pose difficulties with certain types of treatment. However, they may also provide possibilities of effective tumor treatment for pH-sensitive methods that are capable of delivery of drugs, genetic material, and other chemical entities to these low-pH targets. Such methods of targeting tumor sites in the body may involve carriers that undergo a conformational change and release a drug, genetic material, or other chemical entity as cargo upon encountering a pH change within the body such as the pH change surrounding a tumor.

Efforts have been made to utilize pH-sensitive drug/gene delivery vehicles, such as amphiphilic block peptides (U.S. Patent Application Publication No. US 2010/0286069 A1, Nov. 11, 2010), GALA peptides (*Advanced Drug Delivery Reviews* 56 (2004) 967-985), pH (low) insertion peptide (pHLIP) peptides (PNAS 107 (2010) 4081-4086), and pH sensitive polymers (*Macromolecular Research*, 20 (2012) 224-233). In general, a pH change may induce a configurational change of the delivery vehicle, which will be termed a pH-induced phase transition. These drug delivery/release strategies relying on pH-induced phase transition typically require a pH change several times larger than the one taught here, i.e., their required pH change is typically from neutral pH to pH 4-6. Low pH values of 4-6 are present in some intracellular compartments (such as lysosome and endosome) but not in a typical extracellular environment of tumor; therefore, the current technology (GALA, pHLIP, etc.) is ineffective or less effective for tumor targeting. In addition to the drawback of requiring a large pH change to trigger the phase transition, there are other problems associated with the current technology.

Nanoparticles made of amphiphilic block peptides (with at least one hydrophilic block and at least one hydrophobic block) are intact until they enter cells, where they unfold, i.e., they undergo a phase transition, inside endosomes/lysosomes which provide a sufficiently low pH environment. Therefore, drug uptake is predicated on cell ingestion of nanoparticles, typically involving endocytosis, which is a slow and inefficient process. Moreover, nanoparticles made of amphiphilic block peptides are large, typically ~200 nm, thus easily lost to reticuloendothelial system during blood circulation.

GALA is a membrane-perturbing peptide, each forming a helix from a random coil upon a pH change, and together several helices self organize to form a tubule with an inner pore channel at low pH. In this configuration, GALA can penetrate cell membrane's bilayer and transport substance through the pore channel. However, since each helix must have a minimum length to span the thickness of the bilayer, and several helices are required to form a pore channel, GALA is a relatively large peptide (30 amino acids), which adds to the cost of synthesis.

pHLIP are peptides that become hydrophobic at low pH, thus with a tendency to adhere to the cell membrane. Since it is hydrophilic at a neutral pH and often lacking positive charge, it does not afford protection to enzyme-vulnerable amino-add drugs, genes, DNA, RNA, siRNA and smRNA, which are easily attacked by serum enzyme proteins during blood circulation. In general, peptide-digesting serum enzymes thrive in the hydrophilic environment.

Lastly, pH sensitive polymers typically contain segments that are difficult to digest or immune to enzyme-mediated degradation, thus biosensitive or toxic.

Therefore, there is a need for non-toxic and easily synthesized highly pH sensitive delivery vehicles that can protect drugs, dissolve in an extracellular environment in tumor, and release drug.

SUMMARY OF THE INVENTION

A peptide comprising one or more peptide subblocks is provided. Each of the one or more peptide subblocks comprises an amino acid sequence and a linker. The amino acid sequence comprises one or more histidines and one or more nonpolar amino acids. The peptide is sensitive to a pH change.

The peptide may be soluble in an aqueous solution at a pH below 7.0. The peptide may be insoluble in an aqueous solution at a pH of 7.0-8.0.

The amino acid sequence in each subblock contains 2-7 amino acids, 1-5 histidines, and 1-5 nonpolar amino acids. The nonpolar amino acids may be selected from the group consisting of alanine (A), cysteine (C), glycine (G), isoleucine (I), leucine (L), methionine (M), phenylalanine (F), proline (P), tryptophan (W), and valine (V).

The linker in each subblock may be an amino acid, which may be selected from the group consisting of alanine (A), cysteine (C), and glycine (G). The linker may be an alkyl chain having 3-8 carbons.

The peptide may be conjugated to a hydrophilic block. The peptide may be conjugated to a functional block.

A nanoparticle is also provided. The nanoparticle comprises one or more peptides of the present invention. The nanoparticle is sensitive to a pH change. The nanoparticle may be insoluble in an aqueous solution at a pH of 7.0-8.0.

The nanoparticle may further comprise a biologically active substance. The biologically active substance may be a drug selected from the group consisting of DNA, RNA, siRNA, miRNA, drugs, and imaging agents.

The nanoparticle may further comprise a hydrophobic substance, and the solubility of the hydrophobic substance in an aqueous solution is enhanced. The hydrophobic substance may be selected from the group consisting of lonidamine, paclitaxel, and bis-2-(5-phenylacetamido-1,2,4-thiadiazol-2-yl)ethyl sulfide 3 (BPTES).

The nanoparticle may further comprise a hydrophilic surface moiety. The hydrophilic surface moiety may be selected from the group consisting of hydrophilic ionic amino acids, nonionic amino acids, peptides, proteins, and polymers.

In the nanoparticle of the present invention, the peptide may be conjugated to a hydrophilic block and/or a functional block.

The nanoparticle of the present invention may comprise one or more peptides with an amino acid sequence selected from the group consisting of HFFHGHFFHGHFFHGKK (SEQ ID NO: 9), Ac-HFFHGHFFHGHFFHGKK-NH2 (SEQ ID NO: 9), HFFHGHFFHGHFFHGHFFHGKK (SEQ ID NO: 10), HFFHGHFHFGHHFFGKK (SEQ ID NO: 11), and KGHFFHGHFFHGHFFH (SEQ ID NO: 8).

A method for delivering the nanoparticle of the present invention to a subject is further provided. The method comprises administering the nanoparticle to the subject. The nanoparticle may further comprise a biologically active substance, which may be delivered to a target location in the subject.

A kit for delivering the nanoparticle of the present invention to a subject is further provided. The kit comprises the nanoparticle. The kit may further comprise a biologically active substance.

DETAILED DESCRIPTION OF THE INVENTION

Figure 1:
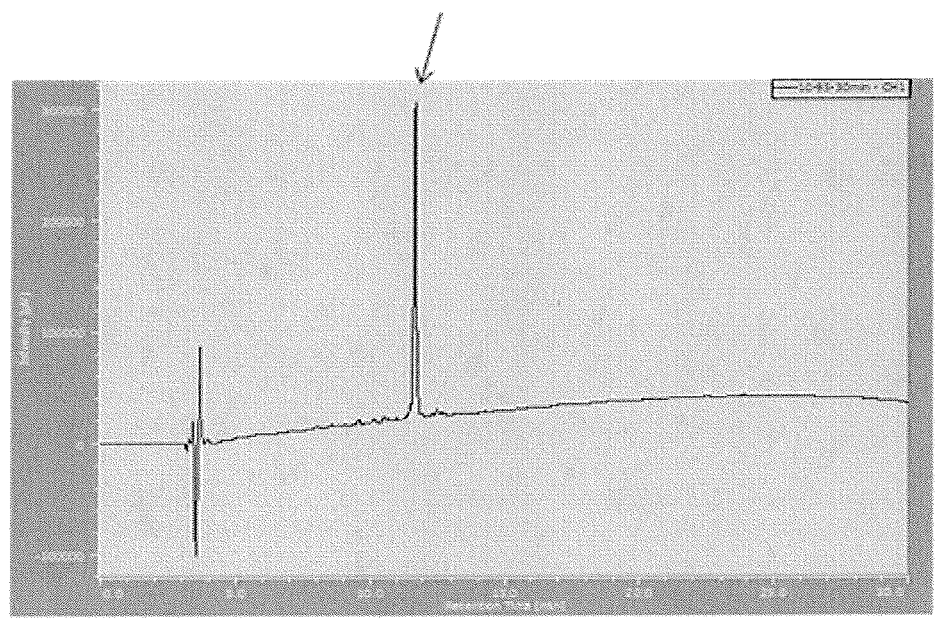
FIG. 1 shows (a) a HPLC peak characteristic of peptide HFFHGHFFHGHFFHGKK (SEQ ID NO: 9) and (b) solubility (in phosphate buffer solution) of nanoparticles at various pH, with a sudden fall at pH 6.9 indicating dissolution of peptide construct from nanoparticle.
Figure 1:
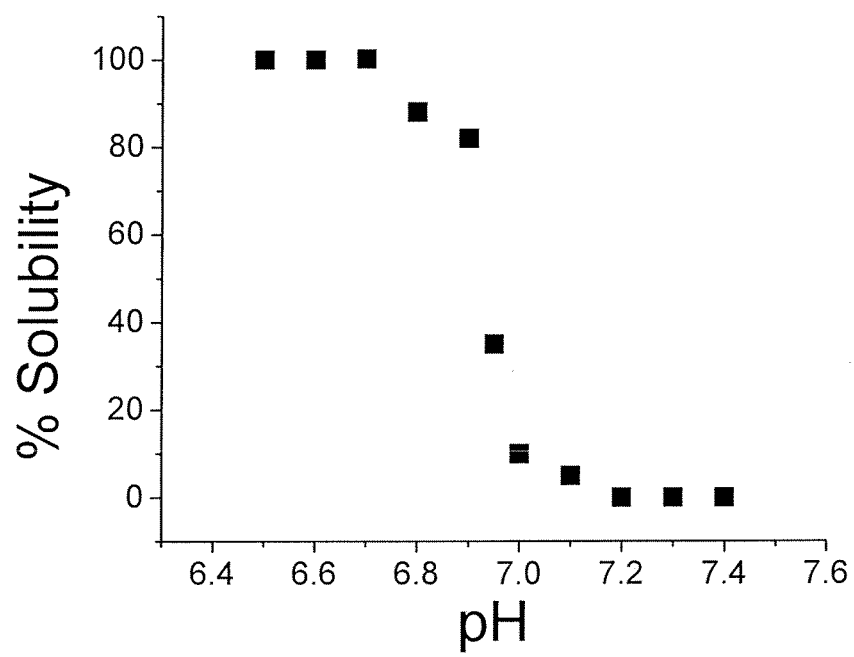

During treatment using pH-sensitive carriers for targeted delivery, certain strategies for drug delivery and release typically rely upon a large change in pH, often from a neutral physiological pH at approximately 7.4 to a significantly lower acidic pH between pH 4 and 6, to release drug and genetic cargoes. These low pH values are present intracellularly in lysosomes and endosomes, but rarely are they present in the extracellular environment of tumors, which tend to have slightly acidic pH in the range from 6 to 7. Therefore, certain carriers will not efficiently release the cargoes in the extracellular environment of tumors, and the release is postponed until the carriers enter the intracellular lysosomes and endosomes. This necessitates intracellular entry, which is a highly inefficient and slow process for certain carriers. Some carriers are large nanoparticles or large peptides which are expensive to synthesize and may be lost to the reticuloendothelial system in blood circulation. Some carriers fail to protect a vulnerable cargo from degradation in the serum of the body. Furthermore, the pH-sensitive carriers used are often immune to degradation within the body and therefore lead to biosensitivity or toxicity.

The present invention relates to pH sensitive short peptides designed and used to form gene/drug containing nanoparticles for delivering gene/drug to targeted locations in human body, including extracellular environment of tumors. These peptides are composed of pH sensitive hydrophilic and hydrophobic (nonpolar) amino acids in the backbone. By wrapping these peptides around cargo and forming a nanoparticle, they provide protection to enzyme-vulnerable substance such as gene, DNA, RNA, siRNA, miRNA, peptides, and other drugs, and shield the cargo from healthy tissues to avoid unintended damage. The present invention also provides highly pH sensitive solubility changes for peptides and their nanoparticles: as the pH environment changes from physiological pH to a weakly acidic condition, the peptides dissolve away from their aggregates/nanoparticles, and the nanoparticles unfold and disintegrates into soluble peptides and soluble peptide aggregates of smaller sizes, exposing and/or releasing the cargo. These solubility changes allow a gene or drug to be securely transported inside the nanoparticle in the blood stream, to be later released at weakly acidic locations such as extracellular environment of tumor sites in the body. The technology described in the present invention has a huge potential for tumor-targeting gene delivery and peptide-drug delivery, which is actively pursued by the pharmaceutical industry and medical research community.

For example, a gene or enzyme may be trapped inside a nanoparticle, and remain stable in the blood stream at nearly neutral physiological pH (pH~7.4); when the nanoparticle breaks down as it enters a more acidic location (pH=6.5~6.9), the gene or enzyme is exposed or released. Since the extracellular pH of normal cells is around 7.4 whereas that of tumors is between 6 and 7 (see review by Danhier et al., "To exploit the tumor microenvironment: Passive and active nanocarriers for anti-cancer drug delivery," *Journal of Controlled Release*, 148 (2010) 135-146), the present invention provides tumor-targeting gene/drug delivery in a simple and general way.

The present invention is based on a novel molecular formulation for pH-sensitive de-novo peptides that form robust nanoparticle carriers for gene and drug delivery for tumor-treating applications. The short peptides taught have many advantages in drug uptake, potency, and non-toxicity. They also have relatively low manufacturing costs. They may further set a new stage for implementing advanced molecular/gene therapy strategies.

The technology described herein concerns short peptides that are highly pH sensitive. For example, in certain embodiment peptides form a nanoparticle at the physiological pH 7-7.4. Prior to their breakdown at the weakly acidic target sites (pH=6.5~6.9), the nanoparticle's interior provides a protective hydrophobic environment for enzyme-vulnerable drugs, gene, DNA, RNA, siRNA and miRNA, which are shielded by the hydrophobic part of the nanoparticle from the hydrophilic environment of serum which hosts enzymes and other serum proteins deleterious for drug/gene delivery. The pH range over which the peptide nanoparticle is stable, and the pH range over which the nanoparticle breaks down, are both adjustable by varying the amino acid sequence in the peptide and the length of the peptide. The peptides in our technology can be made of amino acids of either L form or D form, the former being naturally present in the body. Therefore, once the L-amino-acid-nanoparticle breaks down in the low pH extracellular environment of tumor, the peptide it contains can be easily digested by enzyme, thus engendering little toxicity.

Without being bound by theory, our technology provides several benefits in drug uptake, potency, and non-toxicity. First, once the nanoparticle breakdowns/unfolds at the extracellular environment in the extracellular environment of tumor, the drug is exposed/released and available, so there is no need for endocytosis which is otherwise required for nanoparticle uptake. Second, the exposed drug can be directly absorbed by the cell membrane via various pathways including membrane receptors uptake, which are highly efficient. Third, unlike drugs inside an intact nanoparticle that can only be taken up by one cell, the multitude of molecules of the exposed drug has access to more cells than one, thus the potency is higher. Therefore, pH-triggered nanoparticle meltdown overcomes a key shortcoming of nanoparticle drugs—poor cell-uptake/drug-release. Normal nanoparticle delivery vehicles such as polymerosomes, liposomes, etc. are individually taken up by cells via endocytosis, followed by nanoparticle incorporation into endosomes where nanoparticles are digested to release drugs, which may also digest drugs and rendering them ineffective. Furthermore, the drug molecules released inside endosomes need to later migrate away from the endosomes to become effective. In contrast, the peptide nanoparticles of our invention melt away at the slightly acidic extracellular environment of tumors, releasing the drugs by protonation of peptides. The released drug molecules can be absorbed by many cells, thus vastly increase the bioavailability of drugs and account for the 10× efficacy seen in the in vivo experiment.

The term "peptide" used herein refers to a substantially linear chain of two or more amino acids linked by peptide bonds. A peptide may have about 2, 3, 4, 5, 6, 7, 8, 9, 10, 11, 12, 13, 14, 15, 16, 17, 18, 19, 20, 25, 30, 40, 50, 100, 200 or more amino acids. The amino acids may be L-form or D-form, and may also be modified, deleted, added or substituted. The peptide may comprise one or more amino acids that are glycosylated, acylated, acetylated, carboxylated, and/or hydroxylated. The peptide may comprise one or more side chains. For example, no more than about 50%, preferably no more than about 25%, more preferably no more than about 10%, of the amino acids are in a side chain. A peptide may be obtained using conventional techniques known in the art. For example, a peptide may be synthesized or obtained from a native or recombinant protein by enzymatic digestion.

The term "aqueous solution" used herein refers to a solution in which the solvent is water. Examples of aqueous solution include serum, phosphate buffer solution and water of various pH.

According to the present invention, a peptide comprising one or more peptide subblocks is provided. The peptide subblock comprises an amino acid sequence and a linker. The amino acid sequence comprises one or more histidines and one or more nonpolar amino acids. The peptide is sensitive to a pH change. The peptide may have about 5-50, preferably about 12-23, amino acids.

The term "sensitive to a pH change" used herein refers to a peptide or a nanoparticle that may transit between a hydrophobic state and a hydrophilic state when the pH is changed, for example, in a value of about 2.0, 1.5, 1.0, 0.5, 0.2 or 0.1. For example, a peptide that is sensitive to a pH change may become hydrophilic from hydrophobic when the pH is lowered (e.g., from about 8.0 to about 6.0, or from about 7.4 to about 6.5). The peptide may be hydrophilic at a pH of about 6.0-7.2, preferably about 6.4-7.0, more preferably about 6.5-7.0. The peptide may be hydrophobic at a pH of about 6.8-8.0, preferably about 7.0-8.0, more preferably about 7.1-7.7, most preferably about 7.2-7.5. The peptide may be soluble in an aqueous solution at a pH below 7, and insoluble in an aqueous solution at pH from 7 to 8. These pH ranges for the hydrophilic/hydrophobic transitions, and the corresponding solubility ranges may be adjusted by changing one or more features of the peptide, for example, sequence and length.

The peptide is preferably highly sensitive to a pH change. The term "highly sensitive to a pH change" used herein refers to a peptide or a nanoparticle that may transit between a hydrophobic state and a hydrophilic state when the pH is changed, for example, in a small value of about 1.0, 0.5, 0.2 or 0.1, preferably less than about 0.5, more preferably less than about 0.2, most preferably less than about 0.1. For example, the solubility of the peptide may change from a neutral or weakly basic pH (e.g., about 7.0-7.5) to a weakly acidic pH (e.g., about 6.5-6.9). An insoluble peptide may become soluble in an aqueous solution when the pH of the aqueous solution is lowered by about 1.0, preferably about 0.5, more preferably about 0.3, most preferably about 0.1.

The term "peptide subblock" used herein refers to an entity comprising a short peptide and a linker that exhibits certain structural feature (e.g., being helical or non-helical) or biological function (e.g., being a targeting moiety including but not limited to folate, Arg-Gly-Asp or the so-called RGD, anisamide, mannose and anti-HER2, an imaging agent, or a drug. A peptide subblock may have about 2-7, about 4-6, or about 3-5 amino acids, in addition to a linker. In each peptide subblock, there may be about 1-5, about 2-4, or about 2-3 histidines; about 1-5, about 2-4, or about 2-3 nonpolar amino acids, and a linker made of certain amino acids or alkyl chain. The nonpolar amino acids may be selected from the group consisting of alanine (A), cysteine (C), glycine (G), isoleucine (I), leucine (L), methionine (M), phenylalanine (F), proline (P), tryptophan (W), and valine (V), preferably isoleucine (I), leucine (L), phenylalanine (F), and valine (V). The nonpolar amino acid may be phenylalanine (F). The amino acids in the linker may be selected from the group consisting of alanine (A), cysteine (C), and glycine (G). The amino acids in the linker may be glycine (G). The alkyl chain may contain about 3 to 8, about 3-6, or about 3-5 carbons. Other linkers with similar hydrophobicity/hydrophilicity as the above linker amino acids and linker alkyl chains may also be used. Table 1 provides the standard amino acid abbreviations and properties.

TABLE 1

Standard amino acid abbreviations and properties (Adopted from "Table of standard amino acid abbreviations and properties", in article on "Amino acid", at http://en.wikipedia.org/wiki/Amino_acid.)

| Amino Acid | 3-Letter | 1-Letter | Side-chain polarity | Side-chain charge (pH 7.4) | Hydropathy index |
|---|---|---|---|---|---|
| Alanine | Ala | A | nonpolar | neutral | 1.8 |
| Arginine | Arg | R | Basic polar | positive | −4.5 |
| Asparagine | Asn | N | polar | neutral | −3.5 |
| Aspartic acid | Asp | D | acidic polar | negative | −3.5 |
| Cysteine | Cys | C | nonpolar | neutral | 2.5 |
| Glutamic acid | Glu | E | acidic polar | negative | −3.5 |
| Glutamine | Gln | Q | polar | neutral | −3.5 |
| Glycine | Gly | G | nonpolar | neutral | −0.4 |
| Histidine | His | H | Basic polar | Positive (10%) Neutral (90%) | −3.2 |
| Isoleucine | Ile | I | nonpolar | neutral | 4.5 |
| Leucine | Leu | L | nonpolar | neutral | 3.8 |
| Lysine | Lys | K | Basic polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

TABLE 1-continued

Standard amino acid abbreviations and properties (Adopted from "Table of standard amino acid abbreviations and properties", in article on "Amino acid", at http://en.wikipedia.org/wiki/Amino_acid.)

The peptide of the present invention may comprise two or more peptide subblocks. For example, the peptide may have 2, 3, 4, or 5 peptide subblocks. In the peptide, at least 2 peptide subblocks may be identical, i.e., having identical amino acid sequences, or different, i.e., having different amino acid sequences. For example, in the peptide HFFH-GHFFHGHFFHGKK (SEQ ID NO: 9), there are three identical blocks, each being HFFHG (SEQ ID NO: 12), with G being the linker. In a peptide HFFHGHFFHGHFFH-GHFFHGKK (SEQ ID NO: 10), there are four identical blocks, each being HFFHG (SEQ ID NO: 12), with G being the linker. In HFFHGHFHFGHHFFGKK (SEQ ID NO: 11), there are three independently sequenced subblocks, being HFFHG (SEQ ID NO: 12), HFHFG (SEQ ID NO: 13), and HHFFG (SEQ ID NO: 14), with G being the linker in each subblock.

The peptide may be conjugated to a hydrophilic block. The term "hydrophilic block" used herein refers to a chemical group that prefers (i.e., having a stronger affinity to) water than oil. The hydrophilic block may comprise about 1-5 or about 2-3 hydrophilic amino acids. A hydrophilic amino acid may be acid or basic. For example, the hydrophilic amino acid may be selected from the group consisting of arginine (R), Asparagine (N), aspartate (D), glutamate (E), glutamine (Q), lysine (K), serine (S), threonine (T) and tyrosine (Y). Preferably, the hydrophilic amino acid is aspartate (D) or lysine (K). Preferably, the hydrophilic amino acid is lysine (K). For example, in the peptide HFFHGHFFHGHFFHGKK (SEQ ID NO: 9), the two K forms the hydrophilic block. Likewise, in the peptide KGHFFHGHFFHGHFFH (SEQ ID NO: 8), the hydrophilic block comprises only one K.

The hydrophilic block may comprise a hydrophilic polymer. The term "hydrophilic polymer" used herein refers to a polymer that prefers (i.e., having a stronger affinity to) water than oil. The hydrophilic polymer may be acidic or basic. The hydrophilic polymer may be non-ionic, cationic or anionic.

The peptide may be conjugated to a functional block. The term "functional block" used herein refers to a molecule that provides a chemical or biological function. The biologically active functional block may be selected from the group consisting of folate, Arg-Gly-Asp (RGD), anisamide, mannose, anti-HER2, an imaging agent, a marker, and a drug. The chemical functional group may provide chemical reactivity to the peptide, or to alter its physical properties. Likewise, when peptides become insoluble, as in higher pH, they form nanoparticles, and the chemical functional group may provide reactivity to the nanoparticle, or to alter its physical property, such as stability against aggregation or protein absorption onto nanoparticles. An example of the latter type is polyethylene glycol. The functional block may be attached to the peptide directly or indirectly, for example, by attaching to a hydrophilic block conjugated to the peptide.

A nanoparticle is also provided. The nanopeptide comprises one or more peptides of the present invention. It may additionally comprise a biologically active substance, a hydrophobic substance and/or a hydrophilic surface moiety. Exemplary nanoparticles may have peptides with a sequence selected from the group consisting of HFFHGHFFHGHFF-HGKK (SEQ ID NO: 9), Ac-HFFHGHFFHGHFFHGKK-NH2 (SEQ ID NO: 9), HFFHGHFFHGHFFHGHFFHGKK (SEQ ID NO: 10), HFFHGHFHFGHHFFGKK (SEQ ID NO: 11), and KGHFFHGHFFHGHFFH (SEQ ID NO: 8).

The nanoparticle is sensitive to a pH change. The nanoparticle may change from hydrophobic to hydrophilic when the pH is changed, preferably when the pH is lowered (e.g., from about 8.0 to about 6.0, or from about 7.4 to about 6.5). The nanoparticle may be hydrophilic at a pH of about 6.0-7.2, preferably about 6.4-7.0, more preferably about 6.5-7.0. The nanoparticle may be hydrophobic at a pH of about 6.8-8.0, preferably about 7.0-8.0, more preferably about 7.1-7.7, most preferably about 7.2-7.5. The nanoparticle may be soluble when it is hydrophilic, or insoluble when it is hydrophobic, over the same ranges of pH as described above. For example, the nanoparticle may be soluble in an aqueous solution at a pH below 7, or insoluble in an aqueous solution at a pH from 7 to 8. These pH ranges of the hydrophobic/hydrophilic transition and the corresponding soluble/insoluble transition may be adjusted by changing one or more features of the peptide, e.g., sequence and length.

The nanoparticle is preferably highly sensitive to a pH change. For example, the solubility of the nanoparticle may change from a neutral or weakly basic pH (e.g., about 7.0-7.5) to a weakly acidic pH (e.g., about 6.5-6.9). An insoluble nanoparticle may become soluble in an aqueous solution when the pH of the aqueous solution is lowered by about 1.0, preferably about 0.5, more preferably about 0.3, most preferably about 0.1. These pH ranges of the soluble/insoluble transition may be adjusted by changing one or more features of the peptide, e.g., sequence and length.

The term "biologically active substance" refers to any biological molecule, chemical compound, or a combination thereof that exhibits a biological activity. The biologically active substance may include one vulnerable to enzyme digestion at certain pH, for example, genes, DNA, RNA, siRNA, miRNA, drugs, and imaging agents. The drug may have a therapeutic or diagnostic effect. The biologically active substance may be any therapeutic biological drug, for example, siRNA, lonidamine, and paclitaxel.

The term "hydrophobic substance" refers to any substance whose solubility is greater in a non-polar solvent than that in an aqueous solution. In a nanoparticle comprising a hydrophobic substance according to the present invention, the solubility of the hydrophobic substance in an aqueous solution may be enhanced. The hydrophobic substance may be a biological active substance. Examples of hydrophobic substance include but are not restricted to lonidamine, paclitaxel, and bis-2-(5-phenylacetamido-1,2,4-thiadiazol-2-yl)ethyl sulfide 3 (BPTES).

The term "hydrophilic surface moiety" used herein refers to a substance that has a stronger affinity to water than oil. The hydrophilic surface moiety may be conjugated to the biologically active substance. It may be selected from the group consisting of hydrophilic ionic amino acids, nonionic amino acids, peptides, proteins, and polymers. An example of hydrophilic polymer is polyethylene glycol or dextran. Another example of hydrophilic surface moiety is provided by phospholipid, in which the lipid tail, which is hydrophobic, is incorporated inside the nanoparticle but the phosphate head group, which is hydrophilic, is tethered as a surface moiety on the nanoparticle. A yet another example of hydrophilic surface moiety is PEGylated lipid or PEGylated phospholipid, in which the lipid is incorporated inside the nanoparticle and the PEG is tethered as a surface moiety on the nanoparticle.

In the nanoparticle of the present invention, the peptide may comprise two or more peptide subblocks as described previously. The peptide may be conjugated to a hydrophilic block and/or a functional block.

The nanoparticle of the present invention may be prepared by conventional technologies known in the art. The nanoparticles may be synthesized artificially by chemical synthesis or by recombinant techniques. For example, one or more peptides of the present invention are initially dissolved in an aqueous solution of pH 6.5, then transferred and placed into a solution at a physiological pH between approximately pH 7.0 and 7.4, in which the peptides become insoluble and spontaneously form nanoparticles by self assembly. The solution may further comprise a biologically active substance such that the biologically active substance may be encapsulated or incorporated into the nanoparticles formed by the peptides. The nanoparticles may be formed by injecting a peptide solution using a microfluidic device into a second solution of physiological pH, or by mixing a peptide solution with a second solution of physiological pH again using a microfluidic reactor. Nanoparticles may be synthesized in small quantities or in large amount. They may be synthesized manually in the desired amount suitable for immediate administering to the subject, or in large quantities in large scale chemical reactors. Nanoparticles may be formed by spraying an aerosol of peptide solution into a solution of suitable, neutral to slightly basic solution. Other methods of preparation are also feasible.

For each nanoparticle of the present invention, a method for delivering the nanoparticle is provided. The method comprises administering to the subject the nanoparticle. The nanoparticle comprises one or more peptides of the present invention. The nanoparticle may further comprise a biologically active substance (e.g., a drug), and optionally one or more hydrophilic surface moieties. The method may deliver the biologically active substance to a target location, for example, extracellular environment of solid tumor or tumor cells in peritoneal cavities, in the subject. The amount of the nanoparticles effective for the delivery in a given subject may generally be set by the judgment of a physician. The nanoparticle may separate the biological substance from the biological environment after being administered until reaching a target location, where insoluble nanoparticle becomes soluble and releases the biological substance.

For example, one or more chemical entities may be delivered to a targeted location in a body through a body serum. The method may comprise a series of steps. A nanoparticle may be constructed, comprising a plurality of the peptides of the present invention. Housing the chemical entities, the nanoparticle may be introduced into the body serum for transport through a blood stream of the body. The nanoparticle may maintain its structure in body serum having a physiologically neutral pH of about 7.0-7.4, but break down at body sites having an acidic pH of about 6.5-6.9, such as tumors, releasing the chemical entities.

For each delivery method according to the present invention, a kit is provided. The kit comprises the nanoparticle of the present invention, preferably in an amount suitable for delivery to a target location in a subject. The kit may further comprise a biologically active substance, and optionally a hydrophilic surface moiety. Alternatively, the nanoparticle may comprise a biologically active substance, and optionally a hydrophilic surface moiety. The biological active substance is preferably present in an amount effective to provide a biological activity in the subject, preferably at a target location, when delivered in the nanoparticle.

Example 1

A pH sensitive peptide (Ac-HFFHGHFFHGHFFHGKK-NH$_2$) (SEQ ID NO: 9) was synthesized by the solid phase method. Amino acids blocked by the fluorinylmethyloxycarbonyl (FMOC) group were utilized to couple to a Rink amide resin. Piperideine, N-methylmorpholine (NMM), and hexafluorophosphate (HBTU) in dimethylformamide were used to remove the FMOC group and activate amino acids. The peptide was acetylated with acetic anhydride at the N-terminus and cleaved with trifluoroacetic acid/triisopropylsilane/water (95%/2.5%/2.5%). FIG. 1 (a) shows the HPLC peak characteristic of the peptide. Such peptide spontaneously forms nanoparticles at pH 7.4. The solubility of nanoparticles was measured as a function of pH. As shown in FIG. 1(b), the solubility increases with decreasing pH rendering the peptide and the nanoparticle mostly soluble below pH 6.9 and completely soluble below pH 6.7, from a state of mostly insoluble at pH 7.0 and completely insoluble above pH 7.2. Therefore, there is a sharp transition spanning over a pH interval of only 0.1. The increasing solubility at lower pH is believed to be due to the increasing protonation of the histidine group.

Example 2

Figure 2:
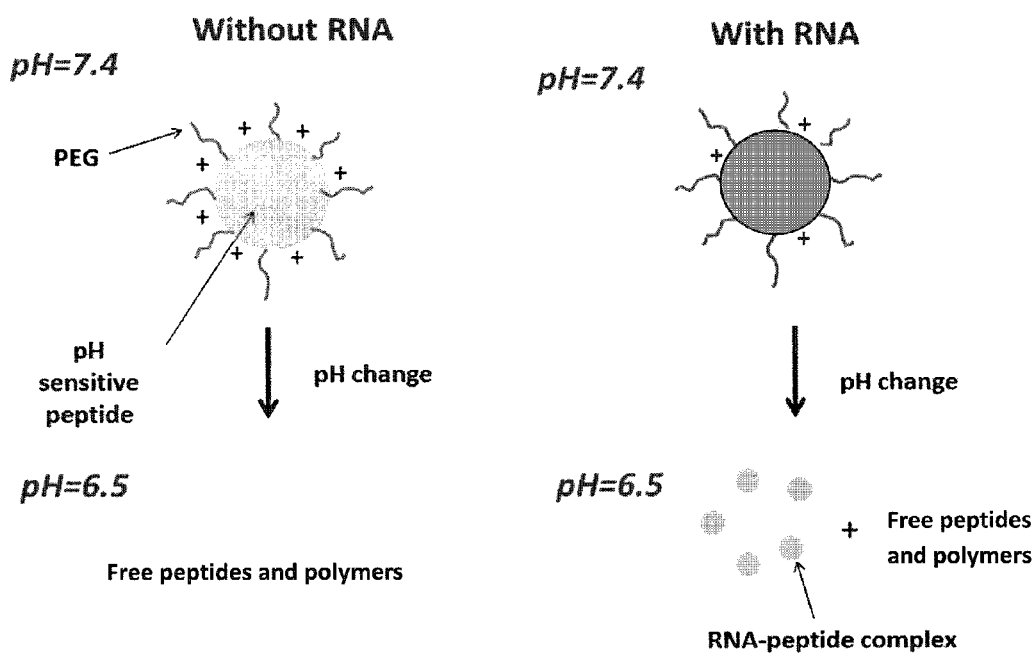
FIG. 2 shows schematic constructs of a pH-sensitive peptide nanoparticle (NP) with RNA (RNA-NP) and without RNA at neutral and weakly acidic pH, in accordance with aspects of the invention.
Figure 3:
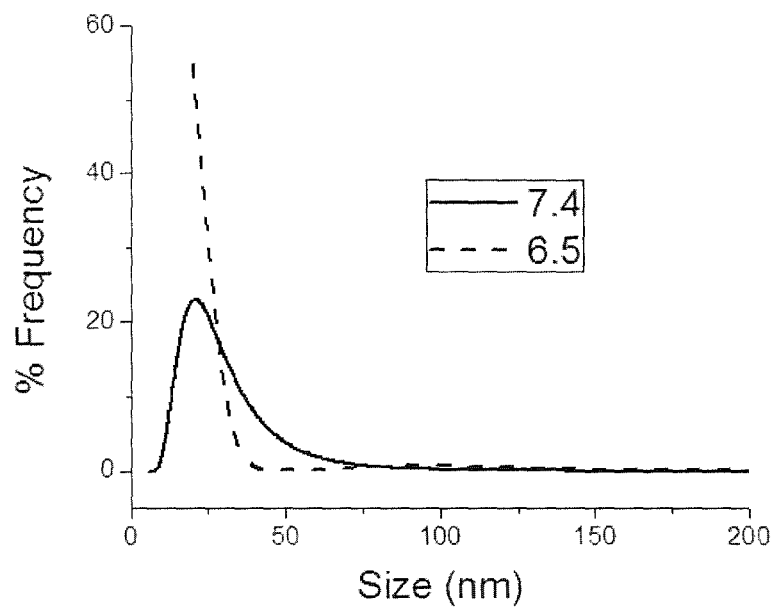
FIG. 3(a) shows particle size distribution of RNA-NP at two pH values. At pH 7.4, the RNA-NP has a well defined size. At pH 6.5, the RNA-NP has disintegrated showing a poorly defined, poly-dispersed range of smaller particles or RNA-complexed peptide constructs.
FIG. 3(b) shows corresponding changes of zeta potential (surface charge) due to protonation of histidines in the peptide constructs of the suspended RNA-peptide complexes.
Figure 3:
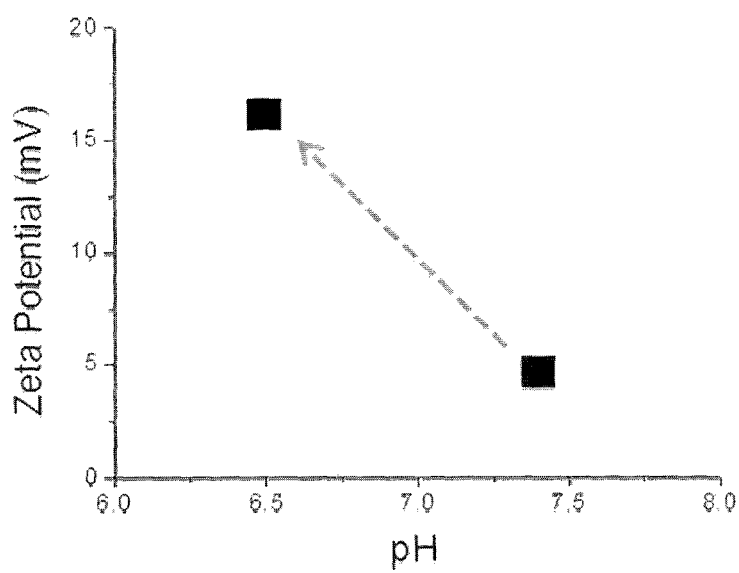

Without being bound by theory, FIG. 2 shows a schematic diagram of the constructs of pH-sensitive nanoparticle (NP) with and without RNA at different pH. Without RNA addition, peptides form nanoparticles at pH 7.4 when peptides are insoluble, and NPs disappear at pH 6.5 when peptides are soluble. With RNA, which is a slightly negatively charged polyanion due to the phosphate group, some peptides are complexed with RNA; then at pH 7.4 when both free peptides and RNA-complexed peptides are insoluble, they form RNA-containing nanoparticles (RNA-NP). The RNA-complexed peptides and uncomplexed peptides dissociate from the nanoparticles at pH 6.5, and exist in the form of smaller RNA-peptide complexes and free uncomplexed peptides. pH sensitive RNA-containing nanoparticles (RNA-NP) of the above type were prepared by mixing RNA with pH sensitive peptide using the following formulation: 90 µl peptide mixture (10 mg/ml, the mixture of peptide of example 1 and 1,2-distearoyl-sn-glycero-3-phosphoethanolamine-N-[carboxy(polyethyleneglycol)-2000 (weight ratio=5:1)), and 10 µl 50 µM siRNA. FIG. 3 shows the change of the size and zeta potential of RNA-NP over pH. RNA-NPs have a well-defined size centered at 20 nm at pH 7.4; at pH 6.5, the size is poorly defined indicating the poly-dispersed nature of smaller particles of RNA-peptide complexes. There is also a large increase of zeta potential (surface charge) as the pH changes from 7.4 to 6.5 due to protonation of histidines in the peptides of the suspended RNA-peptide complexes.

Example 3

Figure 4:
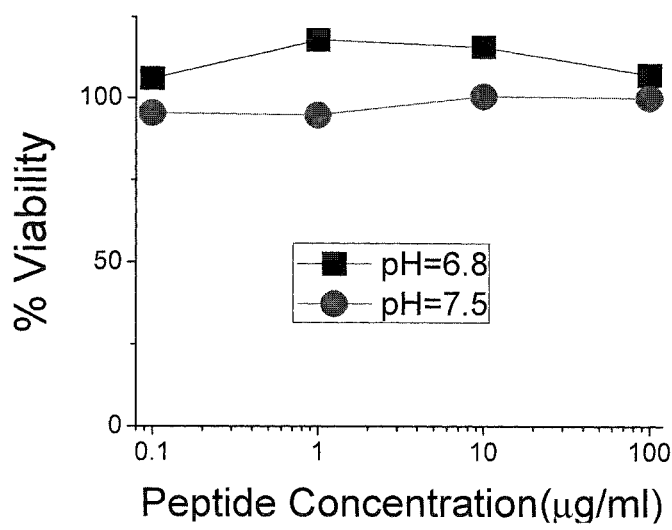
FIG. 4 shows lack of cytotoxicity of a pH sensitive peptide solution for SKOV3 cells. (a) An LDH assay for live cells shows viability remained close to 100% at pH 7.4 (peptide forming nanoparticles) and pH 6.5 (not forming nanoparticles), indicating little cytotoxicity of the peptide. (b) Intensity of LDH release as a marker of dead cells at pH 7.4 and pH 6.5 shows near zero values, indicating indistinguishable from control (set as zero) thus little cytotoxicity of the peptide.
Figure 4:
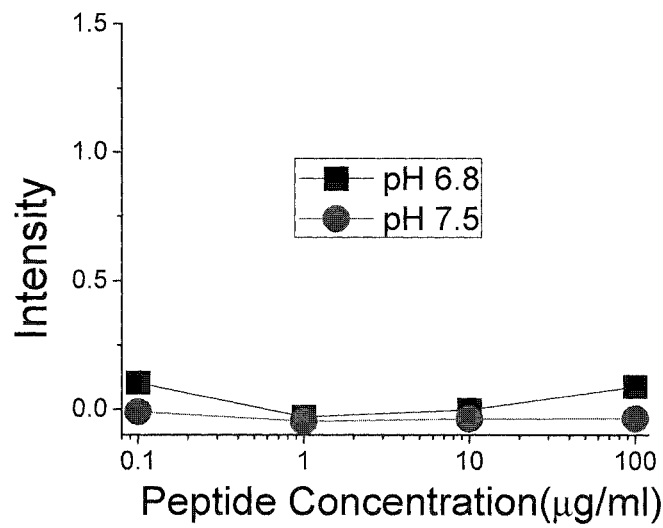

Cytotoxicity, i.e., the effect of peptide on tumor cell viability, was determined using lactic dehydrogenase (LDH) assay. Cells (SKOV3 cells, a human carcinogenic cell line from ovarian cancer) were plated in 96-well plates (10,000 per well for SKOV3) and allowed to adhere overnight at 37° C. in a humidified atmosphere of 5% CO$_2$. Cells were incubated for 3 hours in the DMEM medium containing different concentrations of peptide at pH 6.8 and 7.5, then incubated for additional 24 hours after replacing the culture medium by fresh culture medium. The medium was next removed, the LDH assay lysis solution was added, and the wells were kept at 37° C. for another 45 minutes. Finally, the LDH assay mixture was added and the wells were held at room temperature for still another 20-30 minutes before the absorbance was spectrophotometrically measured at a wavelength of 490 nm on a SpectraMax (Molecular Devices). FIG. 4 shows the cell viability remained close to 100% (upper panel) at both pH 7.4 and pH 6.8, indicating little cytotocixity of the peptide. This was confirmed by the spectrophotometric intensity of dead cells, shown in the lower panel, which was near zero, meaning it is indistinguishable from that of the control. Therefore, the peptide itself is non-toxic and biocompatible.

Example 4 pH sensitive uptake of RNA-NP (prepared per procedure described in Example 2) by tumor cells was evaluated using fluorescent RNA (TEX615-dsRNA, Integrated DNA Technologies, Inc) as a marker for RNA. SKOV3 cells were plated in 12 well plate (48,000 cells per well) and allowed to adhere overnight at 37° C. After incubation for 1 hr with the RNA-NP (containing 5 nM fluorescent RNA) at pH 6.8 and pH 7.5, cells were washed and fixed for imaging. Fluorescence images found, at pH 6.8, RNA (which appeared red) residing in the cells (which were identified by cell nuclei stained in blue), thus confirming RNA uptake inside the cells. In contrast, at pH 7.4, little RNA uptake was detected according to the fluorescence images.

Example 5

Stability of RNA in the form of free RNA and RNA-NP (prepared per procedure described in Example 2) was evaluated using Ribonuclease (RNase). 90 µls of free RNA and RNA-NP (0.5 µM RNA) were incubated with 10 µl RNase (1 mg/ml). After 1 hour incubation at 37° C., samples treated by sodium dodecyl sulfate (SDS) were analyzed using electrophoresis with 5% agarose gel to identify RNA through its electrophoresis mobility of the free RNA and RNA-NP. The results found an RNA band in the RNA-NP sample, but no such band in the free RNA sample, indicating RNA-NP protected RNA from RNase but free RNA was digested by RNase. Therefore, by providing a hydrophobic interior in the nanoparticle for RNA, the pH sensitive peptides can protect RNA from the enzyme outside (in the hydrophilic environment).

Example 6

Silencing of green fluorescent protein (GFP) in GFP-expressed SKOV3 cells (GFP-SKOV) by RNA-NP (prepared per procedure described in Example 2) was demonstrated using EGFP-RNA, a GFP-silencing RNA. GFP-SKOV3 cells were plated in 96 well plate (8,000 cells per well) and allowed to adhere overnight at 37° C. After incubation for 3 hours with RNA-NP (containing 5 nM EGFP-RNA) at pH 6.8, the cells were incubated with fresh cell culture medium for 48 hours. Comparison of the fluorescence images of the GFP-expressed cells without RNA-NP and with RNA-NP found prominent green fluorescence in cells without RNA-NP but very weak or no green fluorescence in cells with RNS-NP. This indicates GFP silencing is due to RNA-NP, which is uptaken by the cell and its EGFP-RNA is transfected to GFP in the cell.

Example 7

Figure 5:
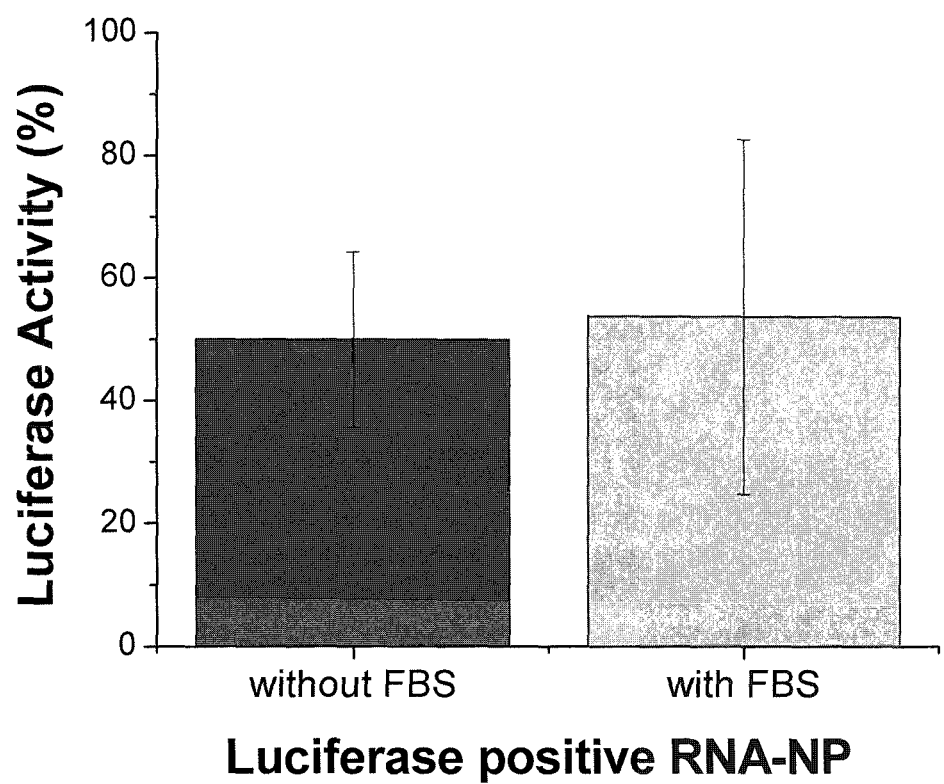
FIG. 5 shows luciferase activity for gene silencing in Luc-SKOV3 cells treated by RNA-NPs. Cells were incubated at pH 6.8 for 24 hours without fetal bovine serum (FBS) and with FBS.

Silencing of luciferase protein (Luc) in Luc-expressed SKOV3 cells (Luc-SKOV) by RNA-NP (prepared per procedure described in Example 2) was demonstrated using FLuc-RNA, a Luc-silencing RNA. Luc-SKOV3 cells were plated in 12-well plate (48,000 cells per well) and allowed to adhere overnight at 37° C. The cells were incubated for 24 hours with RNA-NP (containing 30 pmol Luc-RNA/well) in cell culture media (pH 6.8, with and without 10% Fetal Bovine Serum (FBS)). After the cells were lysed, 20 μl of the lysed solution was transferred to 96-well plate and the luciferase activity was measured by a luminometer after adding 100 μl of luciferase assay reagent. FIG. 5 shows luciferase activity of the Luc-expressed cells with FLuc-RNA-NP. There is a significant (~50%) decrease of luciferase protein indicating Luc silencing due to RNA-NP has occurred with and without FBS. Therefore, RNA delivered by RNA-NP has been uptaken by the cell and its FLuc-RNA transfected to Luc in the cell.

Example 8

Figure 6:
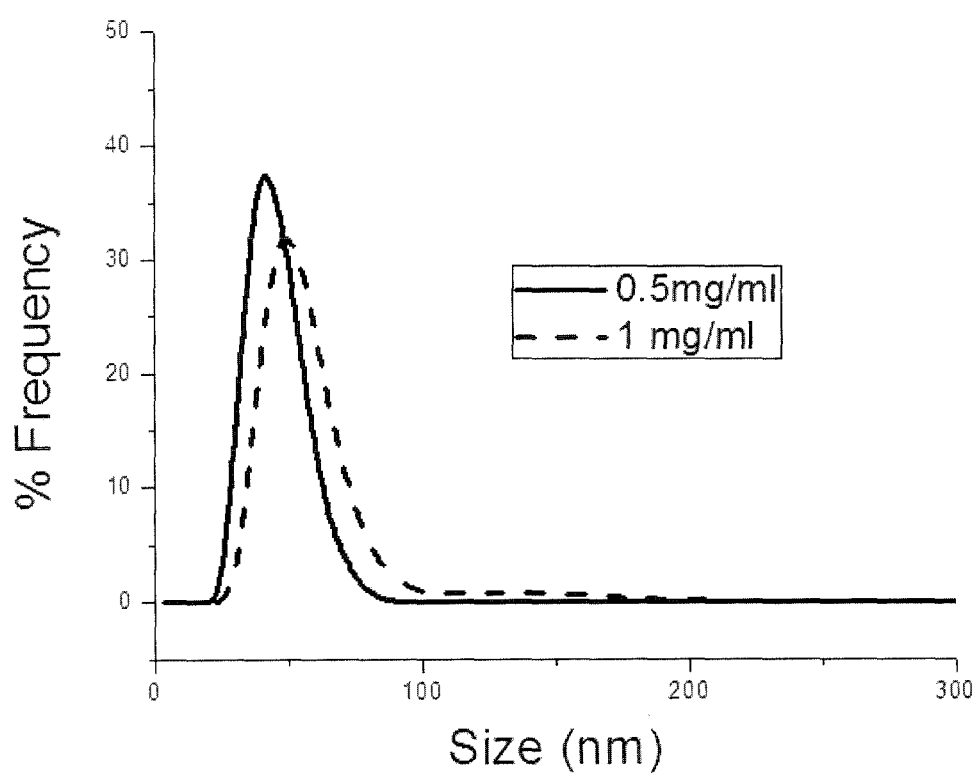
FIG. 6 shows particle size distribution of lonidamine (LND)-containing nanoparticles (LND-NPs) at two LND loading concentrations at pH 7.5.
Figure 7:
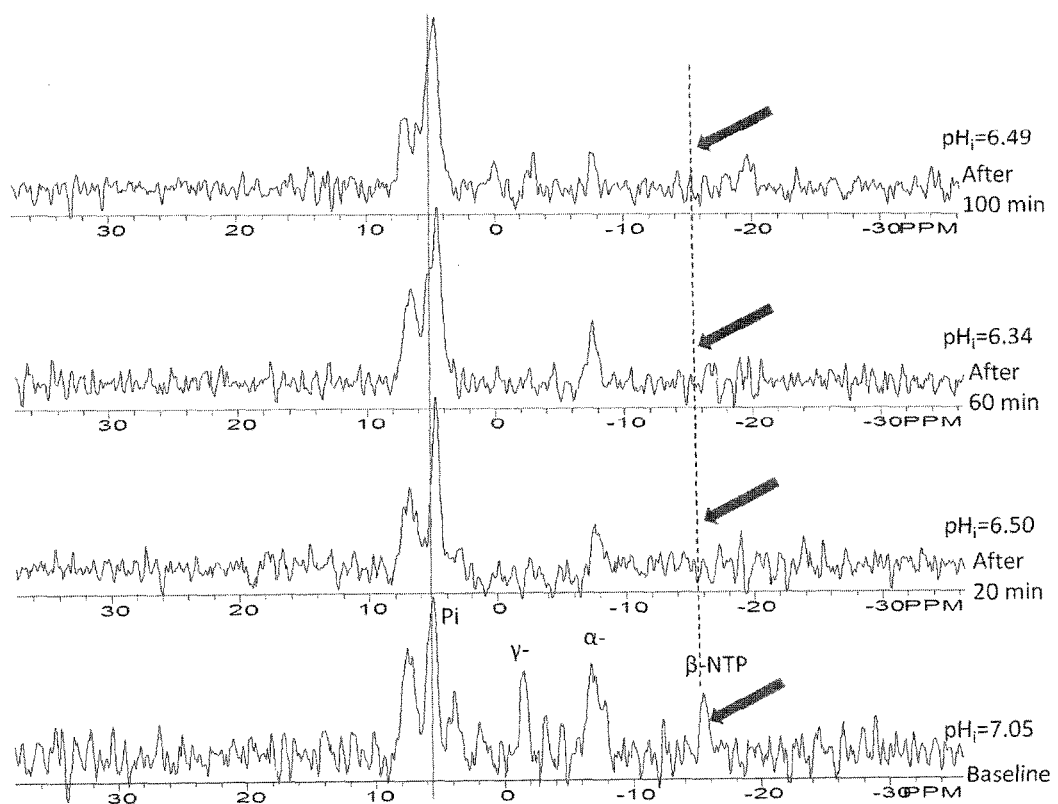
FIG. 7 shows in vivo tumor-localized $^{31}$P-MR spectra acquired at baseline and after injection of LND-NPs (lonidamine-containing nanoparticles), causing pH changes of 0.5 unit (pH values given on the right of the data traces) and reduction of all ($\alpha$, $\beta$, $\gamma$) NTP signals (see labels at bottom; $\beta$-NTP peak marked by arrows and dotted line as guide for eye).

In addition to RNA, pH sensitive nanoparticles can be used to incorporate molecular drugs; one such example is provided by lonidamine. Lonidamine (LND) is a drug that weakens the cells by causing acidification of intracellular pH and de-energization through glucose accumulation and suppression of ATP-powered drug-efflux pumping. Therefore, lonidamine can potentiate various chemotherapy drugs. Because of poor water solubility, however, lonidamine cannot be injected into blood stream, making its delivery difficult. pH sensitive lonidamine-containing nanoparticles (LND-NP) were prepared using the following procedure: pH sensitive peptide (4 mg, 8 mg) of example 1, 1,2-distearoyl-sn-glycero-3-phosphoethanolamine-N-[carboxy(polyethyleneglycol)-2000] (1 mg, 2 mg) and lonidamine (0.5 mg, 1 mg) were dissolved in methanol and dried in $N_2$ gas to form thin film. To the thin film, 1 ml of Phosphate Buffer Solution (PBS) was added and the mixture was sonicated to get 0.5-1 mg lonidamine/ml solution. FIG. 6 shows the sizes of LND-NPs containing different concentrations of lonidamine (0.5, 1 mg/ml). The LND-NPs containing 1 mg LND/ml were injected intravenously into nude mice and induced a complete deprivation of tumor energy (β-NTP) and intracellular acidification that lasted over 100 minutes after injection (FIG. 7). Importantly, such dramatic effect was achieved at 1/10 of the LND dose used for a previous study in which LND was formulated in tris-glycine buffer and injected intraperitoneally at 100 mg/kg (NMR in Biomedicine. 2013; 26(1):98-105). Therefore, LND has been delivered in vivo by the pH-sensitive LND-NP to tumor through blood circulation, and the facile uptake of LND into the cells have resulted in a potent intracellular modulation effect that is witnessed by in vivo measurement.

Example 9

Figure 8:
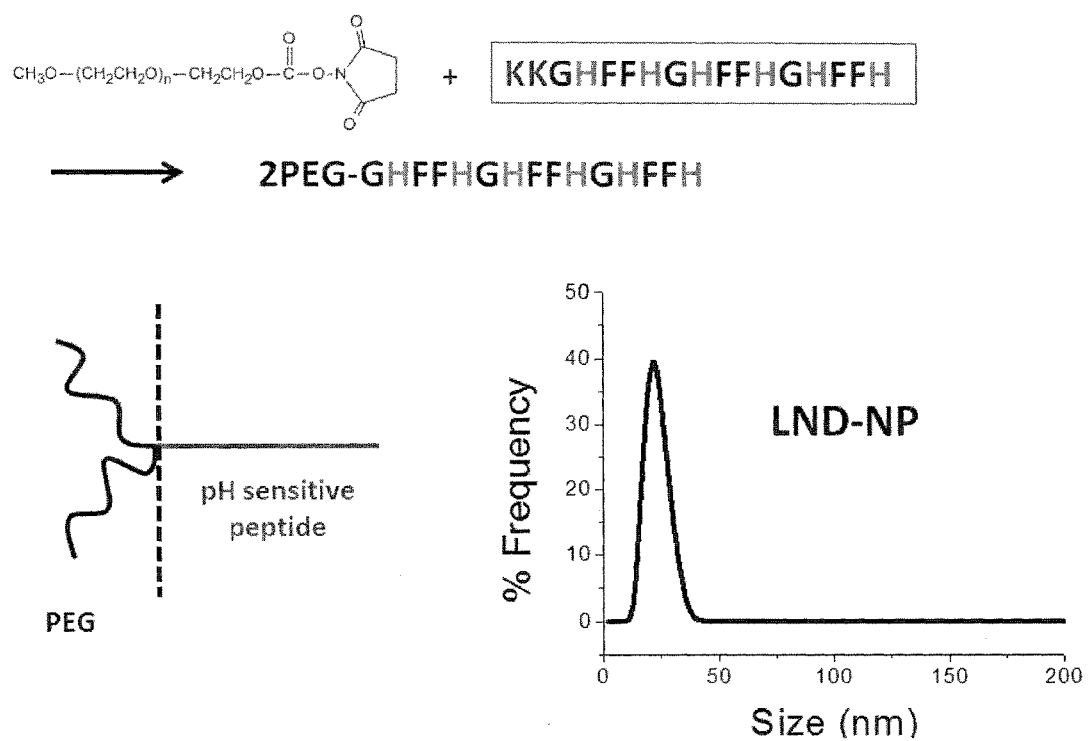
FIG. 8 shows a schematic description of peptide conjugation with PEG and the size distribution of the LND-nanoparticles (LND-NP) containing such peptide and LND at pH 7.5 with an average size ~25 nm.
Figure 9:
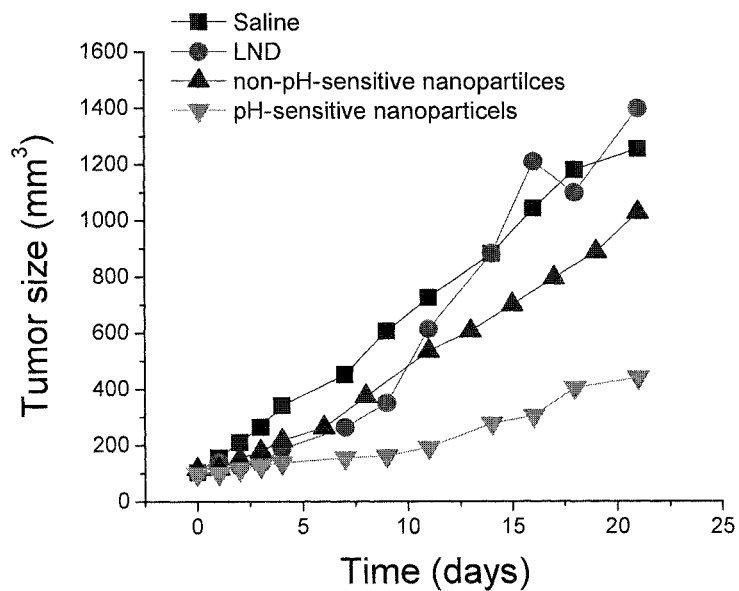
FIG. 9 shows (upper panel) tumor growth and (lower panel) body weight change in mice treated by (i) pH-sensitive nanoparticles: which are LND-NP described in FIG. 11 (dosage=10 mg LND/kg-mouse-weight, administered via intravenous injection), (ii) by non-pH-sensitive nanoparticles: which are LND-containing nanoparticles made of peptides that are not sensitive to pH (dosage=10 mg LND/kg-mouse-weight, administered via intravenous injection), by (iii) LND: which is LND emulsified in a tris-glycine buffer (dosage=100 mg LND/kg, administered via intraperitoneal injection), and by (iv) saline: which is control (saline of the same volume, administered via intravenous injection).
Figure 9:
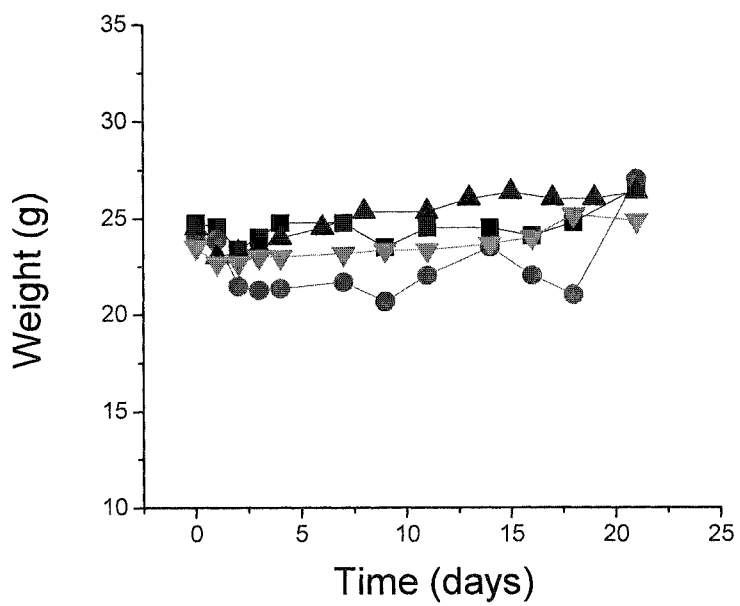

PEG conjugated pH sensitive peptides were prepared for formulating nanoparticles, without using phospholipid as in Example 2. 25 mg of PEG-NHS was conjugated with 10 mg of KKGHFFHGHFFHGHFFH (SEQ ID NO: 15) (also used in Example 1) in a borate buffer solution at pH 8.5 to produce $PEG_2$-GHFFHGHFFHGHFFH (SEQ ID NO: 16). To obtain pH sensitive LND-NP from this PEG-conjugated peptide, with an LND concentration of 1 mg LND/ml, 1 mL of phosphate buffer solution (PBS) was added to the dried film made of LND (1 mg) and $PEG_2$-GHFFHGHFFH-GHFFH (SEQ ID NO: 16) (20 mg) using a similar procedure as in Example 8. This was followed by sonication for 30 min at room temperature. FIG. 8 is a schematic description of peptide conjugation, accompanied by the data of the size distribution of the LND-NP (average is ~25 nm). Suspensions of these pH sensitive LND-NPs were injected into HCC1806 tumor (triple-negative breast cancer, which does not express estrogen receptor, progesterone receptor, and Her2/neu receptor, thus difficult to treat since most therapies target one of these receptors) inoculated mice and tumor growth was monitored over time by measuring the size of the subcutaneous tumor. FIG. 9 shows the tumor growth data in mice treated by this pH-sensitive LND-NP (pH-sensitive nanoparticles; dosage: 10 mg LND/kg-mouse-weight, administered via intravenous injection), by LND emulsified in a tris-glycine buffer (LND; 100 mg LND/kg, administered via intraperitoneal injection), and by control (saline: saline of the same volume, administered via intravenous injection). (The procedure here is similar to that described in Example 8.) In addition, a non-pH sensitive peptide with a pH-insensitive amino-acid sequence was made to similarly form non-pH sensitive LND-containing nanoparticles for comparison at the same LND concentration (non-pH-sensitive nanoparticles; dosage: 10 mg LND/kg-mouse-weight, administered via intravenous injection). The pH-sensitive LND-NP treatment caused a significant delay of tumor growth over 21 days, much more than the LND treatment at 10 times the dosage which caused only a short-term (about 10 days) delay effect compared to the control. Meanwhile, the non-pH sensitive LND-containing nanoparticles only had a small effect. FIG. 9 also shows that over the treatment period, none of the above treatments caused more than 10% weight loss, which is commonly taken as a confirmation of lack of toxicity.

Figure 10:
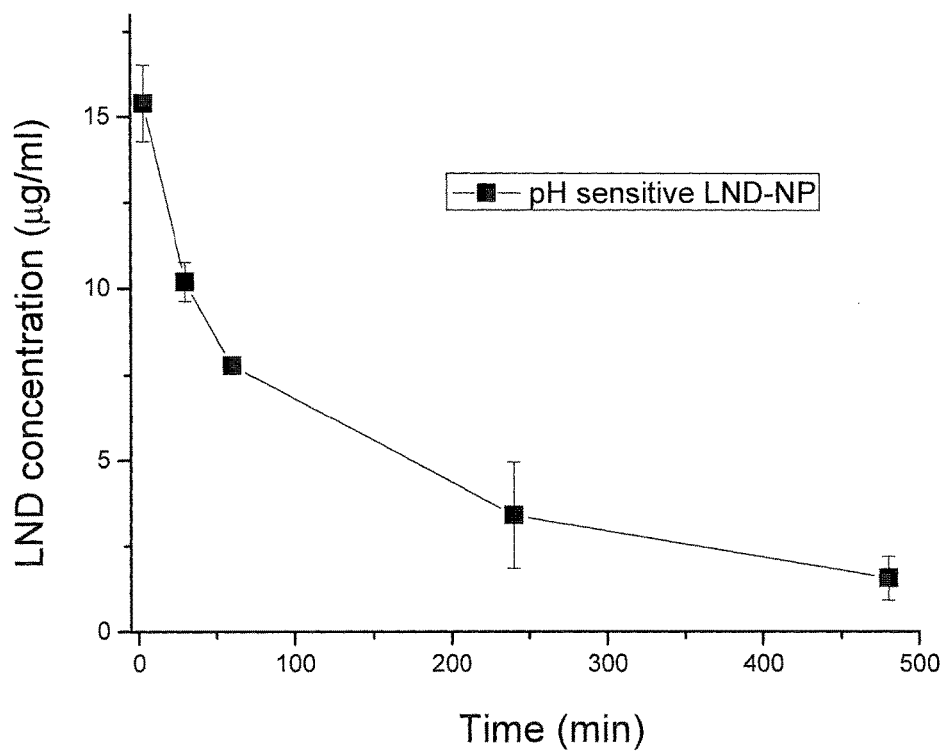
FIG. 10 shows pharmacokinetics of LND-NP nanoparticles of Example 9 in blood circulation (dosage: 10 mg LND/kg-mouse-weight, administered via intravenous injection).
Figure 11:
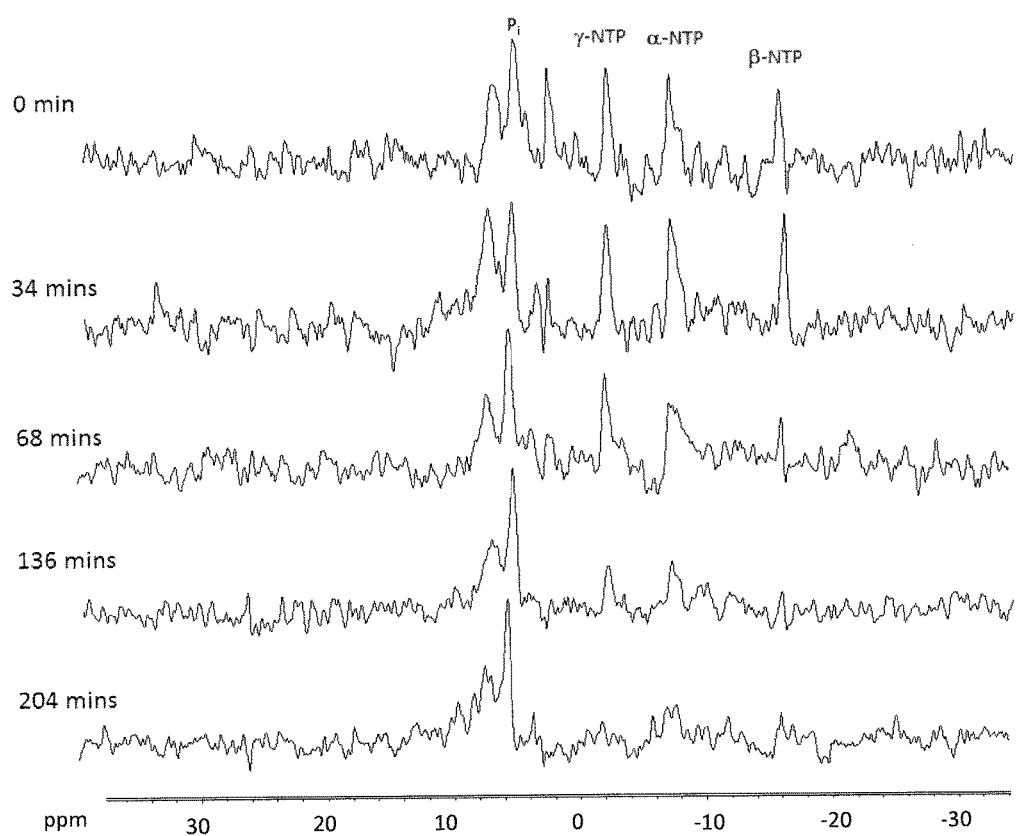
FIG. 11 shows in vivo tumor-localized $^{31}$P-MR spectra acquired at baseline and after injection of LND-NPs of Example 9, which caused reduction of all ($\alpha$, $\beta$, $\gamma$) NTP signals.

The pharmacokinetics of nanoparticles in blood circulation (FIG. 10) was determined after intravenous injection of pH-sensitive LND-NP showing a half-life of LND-NP in blood stream of around 1 hr. Also acquired were in vivo tumor-localized $^{31}$P-MR spectra to indicate the tumor energy change (FIG. 11). The pH-sensitive LND-NP induced a complete deprivation of tumor energy (β-NTP), indicating effective uptake of LND into the tumor.

Example 10

Figure 12:
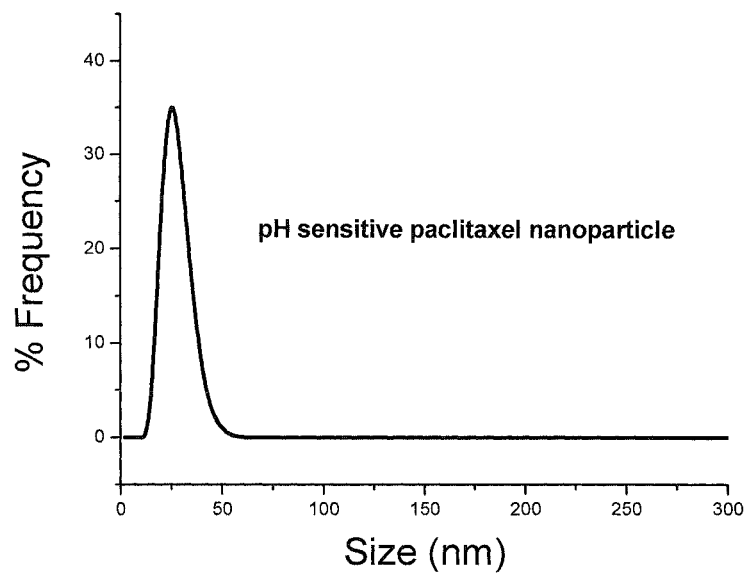
FIG. 12 shows particle size distribution of (a) paclitaxel- and (b) BPTES-containing pH sensitive peptide nanoparticles at pH 7.5, both with an average size ~25 nm.
Figure 12:
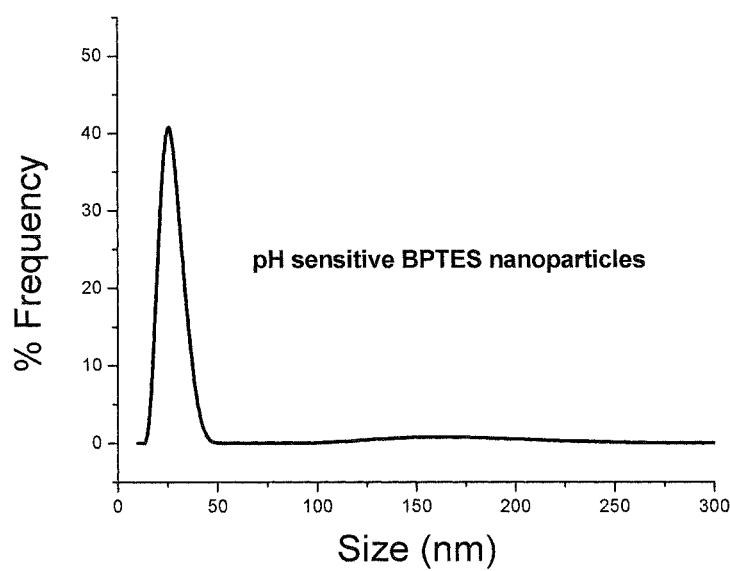

In addition to RNA and LND, other drugs can also be encapsulated in the pH-sensitive nanoparticles using the methods of Example 2 and Example 9. This is illustrated in FIG. 12 for a common chemotherapy drug, paclitaxel (FIG. 12*a*), and a glutaminase inhibiting cancer drug, BPTES (Bis-2-(5-phenylacetamido-1,3,4-thiadiazol-2-yl)ethyl sulfide, FIG. 12*b*). Nanoparticles containing these drugs can be prepared at a size of 25 nm, which is similar to the size of pH-sensitive LND-NP.

Example 11

The concentration of lonidamine (LND) in Example 9 is 1 mg/ml, which is much higher than the solubility of LND in water, about 17 μg/ml. The concentration of paclitaxel in Example 10 is also 1 mg/ml, which is again much higher than the solubility of paclitaxel in water, about 0.3 μg/ml. The concentration of BPTEM in Example 10 is 0.1 mg/ml, which is also much higher than the solubility of BPTES in water, less than, about 1 μg/ml. Therefore, the pH-sensitive peptide may be used in conjunction with a substance of low aqueous solubility, typical for hydrophobic drugs, to enhance their solubility by orders of magnitude. In this sense, it is a potent prodrug. At pH values before the transition, e.g., pH 7.0, the peptide-conjugated drug is fully soluble in aqueous solution.

Example 12

Figure 13:
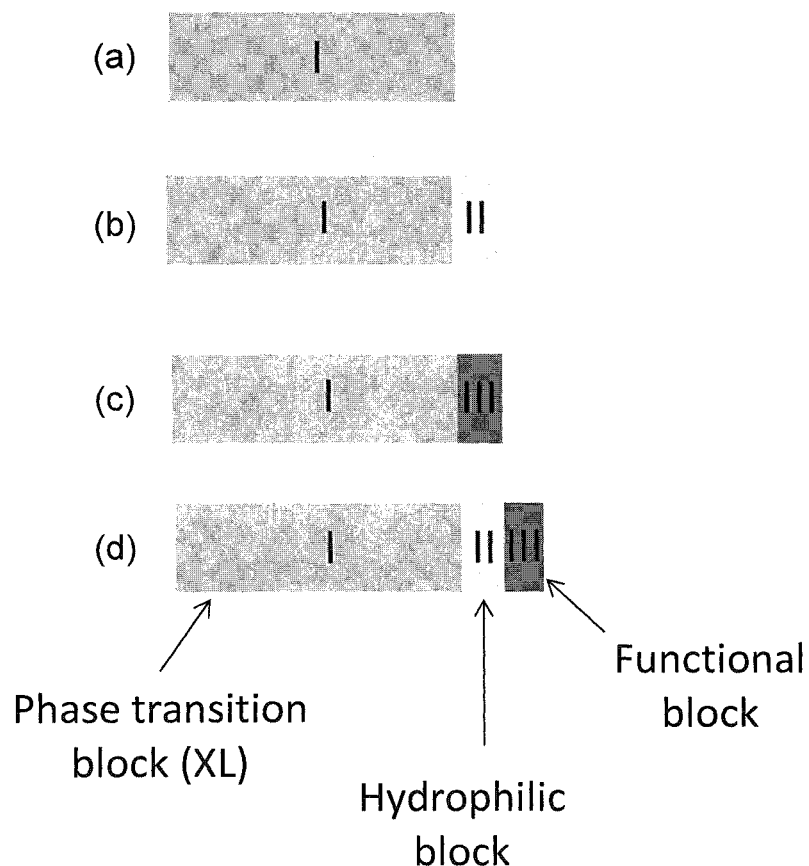
FIG. 13 illustrates four schematic constructs (a-d) of pH sensitive peptides containing a pH-induced-phase-transition block I (comprising of subblock units of XL, where X is a pH-sensitive amino acid sequence and L is a linker), a hydrophilic block II and a functional block III.

A schematic of pH sensitive peptides is described in FIG. 13. In general terms, it may contain three blocks, I, II and III, that have different properties, and are connected in various sequences as exemplified in FIG. 13(a-d). Block I (present in every configuration, FIG. 13(a-d)) is a pH sensitive block entirely or primarily made of pH-sensitive peptides. It comprises of units (i.e., subblocks) of the XL type, where X is a short peptide that is pH sensitive, and L is a linker that may or may not be an amino acid. The entire block I undergoes a pH-induced phase transition. Block II (present in FIG. 13(b, d)) is a hydrophilic block, which may be optionally conjugated to other blocks. Block III (present in FIG. 13(c, d)) is a functional block, which may be optionally conjugated to other blocks. Two 2-block constructs are shown in FIG. 13(b, c), one 3-block example is shown in FIG. 13(d), but other 3-block sequences not shown here are also permissible. Nanoparticles of all four constructs of FIG. 13 are stable at higher pH, and they undergo a pH-induced melting phase transition at lower pH.

Example 13

Five pH sensitive peptides of the following sequences, KGGHFFHGHFFHGK (SEQ ID NO: 17), GHFFHGHFFH (SEQ ID NO: 18), GFFFHGFFFH (SEQ ID NO: 19), GHFFHGFFFH (SEQ ID NO: 20) and KGHFFHGHFFH-GHFFH (SEQ ID NO: 8) were similarly synthesized by the method described in Example (1). Peptides KGGHFFH-GHFFHGK (SEQ ID NO: 17) and GHFFHGHFFH (SEQ ID NO: 18) were soluble at both pH 7.4 and 6.5. Peptides GFFFHGFFFH (SEQ ID NO: 19) and GHFFHGFFFH (SEQ ID NO: 20) were insoluble at both pH 7.4 and 6.5, with GHFFHGFFFH (SEQ ID NO: 20) forming nanoparticles of about 80 nm. Peptide KGHFFHGHFFHGHFFH (SEQ ID NO: 8) was insoluble above about pH 6.7 forming nanoparticles of about 50 nm and soluble below about pH6.7; i.e., it undergoes a pH-induced transition at about pH6.7. Therefore, the pH ranges of the hydrophobic/hydrophilic transition and the corresponding soluble/insoluble transition of peptides and their nanoparticles may be adjusted by changing one or more features of the peptide, e.g., sequence and length, and the hydrophobic block and the functional block to which the peptide is conjugated.

| Peptide | SEQ ID NO |
|---|---|
| HFFH | 1 |
| HFHF | 2 |
| HHFF | 3 |
| FFFH | 4 |
| HFFHGHFFHGHFFHGK | 5 |
| HFFHGHFFHGHFFHGH | 6 |
| HFFHGHFHFGHHFFGK | 7 |
| KGHFFHGHFFHGHFFH | 8 |
| HFFHGHFFHGHFFHGKK | 9 |
| HFFHGHFFHGHFFHGHFFHGKK | 10 |
| HFFHGHFHFGHHFFGKK | 11 |
| HFFHG | 12 |
| HFHFG | 13 |
| HHFFG | 14 |
| KKGHFFHGHFFHGHFFH | 15 |
| GHFFHGHFFHGHFFH | 16 |
| KGGHFFHGHFFHGK | 17 |
| GHFFHGHFFH | 18 |
| GFFFHGFFFH | 19 |
| GHFFHGFFFH | 20 |

The term "about" as used herein when referring to a measurable value such as an amount, a percentage, and the like, is meant to encompass variations of ±20% or ±10%, more preferably ±5%, even more preferably ±1%, and still more preferably ±0.1% from the specified value, as such variations are appropriate. A nanoparticle as used herein may refer to a plurality of nanoparticles, and a peptide as used herein may refer to a plurality of peptides, as such usages are appropriate.

All documents, books, manuals, papers, patents, published patent applications, guides, abstracts, and other references cited herein are incorporated by reference in their entirety. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed:

1. A peptide comprising one or more peptide subblocks, wherein each of the one or more peptide subblocks comprises an amino acid sequence and a linker, wherein the amino acid sequence is selected from the group consisting of HFFHGHFFHGHFFHGKK (SEQ ID NO: 9), Ac-HFFH-GHFFHGHFFHGKK-NH2 (SEQ ID NO: 9), HFFHGHFF-HGHFFHGHFFHGKK (SEQ ID NO: 10), HFFHGHFHF-GHHFFGKK, and KGHFFHGHFFHGHFFH (SEQ ID NO: 8).

2. The peptide of claim 1, wherein the peptide is soluble in an aqueous solution at a pH below 7.0.

3. The peptide of claim 1, wherein the peptide is insoluble in an aqueous solution at a pH of 7.0-8.0.

4. The peptide of claim 1, wherein the linker is an amino acid.

5. The peptide of claim 1, wherein the linker is selected from the group consisting of alanine (A), cysteine (C), and glycine (G).

6. The peptide of claim 1, wherein the linker is an alkyl chain having 3-8 carbons.

7. The peptide of claim 1, wherein the peptide is conjugated to a hydrophilic block.

8. The peptide of claim 1, wherein the peptide is conjugated to a functional block.

9. A nanoparticle comprising one or more peptides of claim 1, wherein the nanoparticle is sensitive to a pH change.

10. The nanoparticle of claim 9, wherein the nanoparticle is insoluble in an aqueous solution at a pH of 7.0-8.0.

11. The nanoparticle of claim 9, wherein the nanoparticle is soluble in an aqueous solution at a pH below 7.0.

12. The nanoparticle of claim 9, further comprising a biologically active substance.

13. The nanoparticle of claim 12, wherein the biologically active substance is a drug selected from the group consisting of DNA, RNA, siRNA, miRNA, drugs, and imaging agents.

14. The nanoparticle of claim 12, further comprising a hydrophilic surface moiety.

15. The nanoparticle of claim 14, wherein the hydrophilic surface moiety is selected from the group consisting of hydrophilic ionic amino acids, nonionic amino acids, peptides, proteins, and polymers.

16. The nanoparticle of claim 9, wherein the peptide is conjugated to a hydrophilic block.

17. The nanoparticle of claim 9, wherein the peptide is conjugated to a functional block.

18. The nanoparticle of claim 9, wherein the amino acid sequence is selected from the group consisting of HFFH-GHFFHGHFFHGKK (SEC) ID NO: 9), Ac-HFFHGHFFH-GHFFHGKK-NH2 (SEQ ID NO: 9), and KGHFFHGHFF-HGHFFH (SEQ ID NO: 8).

19. A method for delivering the nanoparticle of claim 9 to a subject, comprising administering the nanoparticle to the subject.

20. The method of claim 19, wherein the nanoparticle further comprises a biologically active substance, whereby the biological active substance is delivered to a target location in the subject.

21. A kit for delivering the nanoparticle of claim 9 to a subject, comprising the nanoparticle.

22. The kit of claim 21, further comprising a biologically active substance.

23. The peptide of claim 1, wherein the peptide is soluble in an aqueous solution at a pH below 6.8.

24. The peptide of claim 1, wherein the peptide is insoluble in an aqueous solution at a pH of 6.8-8.0.

25. The nanoparticle of claim 9, wherein the nanoparticle is insoluble in an aqueous solution at a pH of 6.8-8.0.

26. The nanoparticle of claim 9, wherein the nanoparticle is soluble in an aqueous solution at a pH below 6.8.

27. The peptide of claim 1, wherein the peptide is soluble in an aqueous solution at a pH below 7.2.

28. The peptide of claim 1, wherein the peptide is insoluble in an aqueous solution at a pH of 7.2-8.0.

29. The nanoparticle of claim 9, wherein the nanoparticle is insoluble in an aqueous solution at a pH of 7.2-8.0.

30. The nanoparticle of claim 9, wherein the nanoparticle is soluble in an aqueous solution at a pH below 7.2.

31. The peptide of claim 1, wherein the peptide is soluble in an aqueous solution at a pH below 6.6.

32. The peptide of claim 1, wherein the peptide is insoluble in an aqueous solution at a pH of 6.6-8.0.

33. The nanoparticle of claim 9, wherein the nanoparticle is insoluble in an aqueous solution at a pH of 6.6-8.0.

34. The nanoparticle of claim 9, wherein the nanoparticle is soluble in an aqueous solution at a pH below 6.6.

35. The nanoparticle of claim 9, further comprising a hydrophobic substance, wherein the solubility of the hydrophobic substance in an aqueous solution is enhanced.

36. The nanoparticle of claim 35, wherein the hydrophobic substance is selected from the group consisting of lonidamine, paclitaxel, and bis-2-(5-phenylacetamido-1,2,4-thiadiazol-2-yl)ethyl sulfide 3 (BPTES).

37. The peptide of claim 1, wherein the amino acid sequence is selected from the group consisting of HFFH-GHFFHGHFFHGKK (SEQ ID NO: 9), Ac-HFFHGHFFH-GHFFHGKK-NH2 (SEQ ID NO: 9), and KGHFFHGHFF-HGHFFH (SEQ ID NO: 8).

* * * * *

UNITED STATES PATENT AND TRADEMARK OFFICE
CERTIFICATE OF CORRECTION

PATENT NO.       : 9,687,563 B2
APPLICATION NO.  : 14/914787
DATED            : June 27, 2017
INVENTOR(S)      : I-Wei Chen et al.

Page 1 of 1

It is certified that error appears in the above-identified patent and that said Letters Patent is hereby corrected as shown below:

At Column 24, Line 30, "(SEC) ID NO: 9)," should read -- (SEQ ID NO: 9), --

Signed and Sealed this
Third Day of October, 2017

Joseph Matal
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 20

<210> SEQ ID NO 1
<211> LENGTH: 4
<212> TYPE: PRT
<213> ORGANISM: Artificial Sequence
<220> FEATURE:
<223> OTHER INFORMATION: Synthetic

<400> SEQUENCE: 1

His Phe Phe His
1

<210> SEQ ID NO 2
```

```
<211> LENGTH: 4
<212> TYPE: PRT
<213> ORGANISM: Artificial Sequence
<220> FEATURE:
<223> OTHER INFORMATION: Synthetic

<400> SEQUENCE: 2

His Phe His Phe
1

<210> SEQ ID NO 3
<211> LENGTH: 4
<212> TYPE: PRT
<213> ORGANISM: Artificial Sequence
<220> FEATURE:
<223> OTHER INFORMATION: Synthetic

<400> SEQUENCE: 3

His His Phe Phe
1

<210> SEQ ID NO 4
<211> LENGTH: 4
<212> TYPE: PRT
<213> ORGANISM: Artificial Sequence
<220> FEATURE:
<223> OTHER INFORMATION: Synthetic

<400> SEQUENCE: 4

Phe Phe Phe His
1

<210> SEQ ID NO 5
<211> LENGTH: 17
<212> TYPE: PRT
<213> ORGANISM: Artificial Sequence
<220> FEATURE:
<223> OTHER INFORMATION: synthetic

<400> SEQUENCE: 5

His Phe Phe His Gly His Phe Phe His Gly His Phe Phe His Gly Lys
1               5                   10                  15

Lys

<210> SEQ ID NO 6
<211> LENGTH: 22
<212> TYPE: PRT
<213> ORGANISM: Artificial Sequence
<220> FEATURE:
<223> OTHER INFORMATION: Synthetic

<400> SEQUENCE: 6

His Phe Phe His Gly His Phe Phe His Gly His Phe Phe His Gly His
1               5                   10                  15

Phe Phe His Gly Lys Lys
            20

<210> SEQ ID NO 7
<211> LENGTH: 17
<212> TYPE: PRT
<213> ORGANISM: Artificial Sequence
<220> FEATURE:
<223> OTHER INFORMATION: Synthetic

<400> SEQUENCE: 7

His Phe Phe His Gly His Phe Phe Gly His His Phe Phe Gly Lys
```

```
1               5                   10                  15
Lys

<210> SEQ ID NO 8
<211> LENGTH: 16
<212> TYPE: PRT
<213> ORGANISM: Artificial Sequence
<220> FEATURE:
<223> OTHER INFORMATION: Synthetic

<400> SEQUENCE: 8

Lys Gly His Phe Phe His Gly His Phe Phe His Gly His Phe Phe His
1               5                   10                  15

<210> SEQ ID NO 9
<211> LENGTH: 17
<212> TYPE: PRT
<213> ORGANISM: Artificial Sequence
<220> FEATURE:
<223> OTHER INFORMATION: Synthetic

<400> SEQUENCE: 9

His Phe Phe His Gly His Phe Phe His Gly His Phe Phe His Gly Lys
1               5                   10                  15

Lys

<210> SEQ ID NO 10
<211> LENGTH: 22
<212> TYPE: PRT
<213> ORGANISM: Artificial Sequence
<220> FEATURE:
<223> OTHER INFORMATION: Synthetic

<400> SEQUENCE: 10

His Phe Phe His Gly His Phe Phe Gly His Phe Phe His Gly His
1               5                   10                  15

Phe Phe His Gly Lys Lys
            20

<210> SEQ ID NO 11
<211> LENGTH: 17
<212> TYPE: PRT
<213> ORGANISM: Artificial Sequence
<220> FEATURE:
<223> OTHER INFORMATION: Synthetic

<400> SEQUENCE: 11

His Phe Phe His Gly His Phe His Phe Gly His His Phe Phe Gly Lys
1               5                   10                  15

Lys

<210> SEQ ID NO 12
<211> LENGTH: 5
<212> TYPE: PRT
<213> ORGANISM: Artificial Sequence
<220> FEATURE:
<223> OTHER INFORMATION: Synthetic

<400> SEQUENCE: 12

His Phe Phe His Gly
1               5

<210> SEQ ID NO 13
<211> LENGTH: 5
```

```
<212> TYPE: PRT
<213> ORGANISM: Artificial Sequence
<220> FEATURE:
<223> OTHER INFORMATION: Synthetic

<400> SEQUENCE: 13

His Phe His Phe Gly
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic

<400> SEQUENCE: 14

His His Phe Phe Gly
1               5

<210> SEQ ID NO 15
<211> LENGTH: 17
<212> TYPE: PRT
<213> ORGANISM: Artificial Sequence
<220> FEATURE:
<223> OTHER INFORMATION: Synthetic

<400> SEQUENCE: 15

Lys Lys Gly His Phe Phe His Gly His Phe Phe His Gly His Phe Phe
1               5                   10                  15

His

<210> SEQ ID NO 16
<211> LENGTH: 15
<212> TYPE: PRT
<213> ORGANISM: Artificial Sequence
<220> FEATURE:
<223> OTHER INFORMATION: Synthetic

<400> SEQUENCE: 16

Gly His Phe Phe His Gly His Phe Phe His Gly His Phe Phe His
1               5                   10                  15

<210> SEQ ID NO 17
<211> LENGTH: 14
<212> TYPE: PRT
<213> ORGANISM: Artificial Sequence
<220> FEATURE:
<223> OTHER INFORMATION: Synthetic

<400> SEQUENCE: 17

Lys Gly Gly His Phe Phe His Gly His Phe Phe His Gly Lys
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Synthetic

<400> SEQUENCE: 18

Gly His Phe Phe His Gly His Phe Phe His
1               5                   10

<210> SEQ ID NO 19
```

```
<211> LENGTH: 10
<212> TYPE: PRT
<213> ORGANISM: Artificial Sequence
<220> FEATURE:
<223> OTHER INFORMATION: Synthetic

<400> SEQUENCE: 19

Gly Phe Phe Phe His Gly Phe Phe Phe His
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Synthetic

<400> SEQUENCE: 20

Gly His Phe Phe His Gly Phe Phe Phe His
1               5                   10
```